(12) United States Patent
Neumann et al.

(10) Patent No.: US 8,716,485 B2
(45) Date of Patent: *May 6, 2014

(54) PYRAZOLE SYNTHESIS BY COUPLING OF CARBOXYLIC ACID DERIVATIVES AND ENAMINES

(75) Inventors: Julia Neumann, Duesseldorf (DE); Mamta Suri, Muenster (DE); Frank Glorius, Ascheberg (DE)

(73) Assignee: Westfälishe Wilhelms-Universität Münster (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/635,112

(22) PCT Filed: Mar. 23, 2011

(86) PCT No.: PCT/EP2011/054484
§ 371 (c)(1),
(2), (4) Date: Sep. 14, 2012

(87) PCT Pub. No.: WO2011/120861
PCT Pub. Date: Oct. 6, 2011

(65) Prior Publication Data
US 2013/0012715 A1    Jan. 10, 2013

(30) Foreign Application Priority Data

Mar. 29, 2010 (DE) .......................... 10 2010 013 282

(51) Int. Cl.
*C07D 231/14* (2006.01)
*C07D 231/12* (2006.01)
*C07D 401/04* (2006.01)
*C07D 405/04* (2006.01)

(52) U.S. Cl.
USPC .................. 546/275.4; 548/365.1; 548/365.7; 548/374.1

(58) Field of Classification Search
None
See application file for complete search history.

(56) References Cited

PUBLICATIONS

L. Yet: Comprehensive Heterocyclic Chemistry III, vol. 4, Albany Molecular Research, Inc., 2008, 73 pages Date: 2008.
J. Elguero: Pyrazoles and their Benzo Derivatives, Instituto de Quimica Medica, Madrid, 22 pages, Date: Jan. 1, 1984.
International Search Report; PCT/EP11/54484; International File Date: Mar. 23, 2011; Westfaelishe Wilhelms—Universitaet Muenster.

*Primary Examiner* — Janet L Andres
*Assistant Examiner* — Timothy R Rozof
(74) *Attorney, Agent, or Firm* — Schmeiser, Olsen & Watts, LLP

(57) ABSTRACT

The invention describes a novel process for synthesizing pyrazoles by means of oxidative conversion of enamines with suitable N-containing carboxylic acid derivatives.

5 Claims, No Drawings

PYRAZOLE SYNTHESIS BY COUPLING OF CARBOXYLIC ACID DERIVATIVES AND ENAMINES

The invention relates to the field of organic synthesis, especially the field of heterocycle synthesis.

Heterocyclic compounds play an immense role in organic chemistry, especially in active ingredients and pharmaceuticals, and the synthesis of heterocyclic compounds represents an important and constantly growing field of research.

Pyrazoles represent an important class of heterocycles. Pyrazoles occur relatively rarely in natural materials, but are an important structural element in biologically active compounds, which in some cases can have great economic importance as pharmaceuticals or plant protecting agents. Two prominent examples are the COX-2 inhibitor Celecoxib, which is used to treat rheumatoid arthritis, and the contact poison Fipronil®, which is effective as a GABA inhibitor against ectoparasites, such as fleas, lice, ticks, and mites.

It is known to the technical expert that pyrazoles can be produced in different ways ("Comprehensive Essay about Pyrazoles," L. Yet, in *Comprehensive Heterocyclic Chemistry III, Vol.* 4 (Eds.: A. R. Katritzky, C. A. Ramsden, E. F. V. Scriven, R. J. K. Taylor), Elsevier, 2008, p. 1-141), among which three methods are the most frequent:

- The Knorr condensation of 1,3-dicarbonyl compounds with hydrazines,
- The 1,3-dipolar cycloaddition of hydrazones to alkynes, and
- The functionalization of preformed pyrazole rings on nitrogen by means of direct alkylation or arylation, whether by means of nucleophilic substitution or by means of modern transition metal-catalyzed carbon-nitrogen bond-forming reaction.

These methods have two fundamental disadvantages: Regioselectivity problems can occur, on the one hand, as soon as different substituents are to be present for the nitrogens especially at the two alpha-position carbon atoms. On the other hand, they need hydrazine substrates, which are generally carcinogenic and not easily available in some cases.

The goal is therefore to create an improved pyrazole synthesis, with which the above disadvantages can be overcome, and which allows a simple, hydrazine-free synthesis of pyrazoles.

This goal is attained by means of a process according to claim 1. A process is accordingly proposed for the production of pyrazoles by converting enamines and N-containing carboxylic acid derivatives in the presence of an oxidizing agent.

It was a surprise to discover that enamines and N-containing carboxylic acid derivatives react by forming pyrazoles in the presence of an oxidizing agent. This process offers in many applications, especially one or more of the following advantages:

- The reagents are stable, common compounds that are easy to obtain,
- The process tolerates many other functional groups,
- A control of the regioisomers (in particular on C-3 and C-5) can be easily carried out because the "N—N" bond is closed,
- The process is also suitable for technical application as a result of the simple performance of the reaction; it can serve for the synthesis of pyrazoles both in milligram and in multigram and kilogram quantities,
- The pyrazole derivatives accessible according to the invention can be utilized for the synthesis of numerous by-products, which are important, for example, as pharmaceuticals for human and veterinary medicine or as plant protection agents,
- The process is robust and not air-sensitive, so that it does not require a protective gas atmosphere,
- As a result of the modularity of the reaction, the substitution pattern can be easily varied by varying one or more components, and component libraries with systemically varied radicals can be generated in this way,
- Pyrazoles can be directly formed from simple, commercially available components (amine, ketone, and nitrile) in a one-pot process.

The term "conversion" in the sense of the invention means in particular that the respective substrates are brought in contact with each other and with an oxidizing agent. This occurs as a rule by means of a mixing or suspension. It should be noted that either of the two educts are made available and then oxidized in dependence upon the concrete embodiment of the process; it can, however, also be advantageous to introduce one educt together with the oxidizing agent and to add the other.

According to a preferred embodiment of the invention, the reaction temperature is between $\geq 0$ and $\leq 200°$, preferably between $\geq 60$ and $\leq 140°$ C., and particularly preferably between $\geq 80$ and $\leq 120°$ C.

Neither the pressure nor the type of gas atmosphere over the reaction is critical, and different gases and pressures are suitable, for example, air, nitrogen, argon, oxygen, preferably air and nitrogen. The reaction can be carried out at different pressures, preferably at pressures of 1 to 10 atm, and particularly preferably at 1 to 4 atm. Increasing the pressure can lead to the increase of the boiling point, which can cause an acceleration of the reaction.

Another object of the invention is also any process in which the reaction product continues to react already under the reaction conditions or by means of a gradual variation of the reaction conditions, for example, by means of a saponification of an ester group, a decarboxylation reaction, or a hydration.

The preparation of the reaction mixture and the purification of the products are usually less critical and are arranged according to the corresponding physical properties of the products and by-products that are generated. Preferred methods for preparation and purification are distillation, sublimation, crystallization, chromatography, filtration, and extraction. Purification is generally simpler in comparison with the previous purification processes and makes it possible to obtain a product with a greater purity, because hydrazines are avoided.

According to a preferred embodiment of the invention, the ratio of enamines to N-containing carboxylic acid derivatives (mol of N-containing carboxylic acid derivatives to mol of enamine) is $\geq 0.2:1$ to $\leq 150:1$, preferably $\geq 1:1$ to $\leq 100:1$, and most preferably $\geq 2:1$ to $\leq 20:1$. The excess of N-containing carboxylic acid derivative can come about, for instance, by the reaction taking place in the N-containing carboxylic acid derivative as solvent. Preferred compounds in this case are especially acetonitrile, propionitrile, isobutyronitrile, butyronitrile, valeronitrile, capronitrile, heptanoic acid nitrile, octanoic acid nitrile, nonanoic acid nitrile, benzonitrile, and their monofluorinated or polyfluorinated straight-chain and branched derivatives.

According to a preferred embodiment of the invention, the reaction takes place in a solvent selected from the group comprising pentane, hexane, heptanes, octane, petroleum ether, toluene, xylenes, chlorobenzene, o-dichlorobenzene, ethyl acetate, tetrahydrofurane, diethyl ether, methyl tert-butyl ether, 1,4-dioxane, N,N-dimethyl formamide, dimethyl sulfoxide, 1,2-dichloroethane, N,N-dimethyl acetamide, dimethoxyethane, or carboxylic acids such as formic acid, acetic acid, trifluoroacetic acid, chloroacetic acid, trichloroacetic acid, propionic acid, butyric acid, or alcohols such as methanol, ethanol, propanol, isopropanol, butanol, t-butanol or phenol, preferably ethyl acetate, tetrahydrofurane, diethyl ether, methyl tert-butyl ether, 1,4-dioxane, N,N-dimethyl formamide, dimethyl sulfoxide, 1,2-dichloroethane, N,N-dimethyl acetamide, t-butanol, chlorobenzene, toluene, dimethoxyethane, hexane, o-dichlorobenzene, especially preferably 1,4-dioxane, N,N-dimethyl formamide, dimethyl sulfoxide, 1,2-dichloroethane, N,N-dimethyl acetamide, t-butanol, and chlorobenzene, or mixtures thereof.

According to a preferred embodiment of the invention, the N-containing carboxylic acid derivatives are selected from the group comprising nitriles, carboxylic acid amides, amidines, imidates, imidoyl chlorides, derived protonated salts of these compounds, as well as mixtures thereof.

Compounds having the following structure are preferably used as enamines:

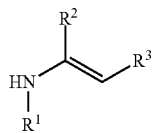

wherein $R^1$, $R^2$, and $R^3$ are selected, independently from one another, from the group comprising hydrogen, hydroxyl, halogen, pseudohalogen, formyl, carboxyl and/or carbonyl derivatives, alkyl, long-chain alkyl, alkoxy, long-chain alkoxy, cycloalkyl, halogen alkyl, aryl, arylenes, halogen aryl, heteroaryl, heteroarylenes, heterocycloalkylenes, heterocycloalkyl, halogen heteroaryl, alkenyl, halogen alkenyl, alkinyl, halogen alkinyl, keto, ketoaryl, halogen ketoaryl, ketoheteroaryl, ketoalkyl, halogen ketoalkyl, ketoalkenyl, halogen ketoalkenyl, phosphoalkyl, phosphonates, phosphates, phosphine, phosphine oxide, phosphoryl, phosphoaryl, sulfonyl, sulfoalkyl, sulfoarenyl, sulfonates, sulfates, sulfones, amines, polyether, silyl alkyl, silyl alkyloxy, wherein one or more of the non-neighboring $CH_2$ groups can be substituted, independently from one another, by means of —O—, —S—, —NH—, —NR°—, —SiR°R°°—, —CO—, —COO—, —OCO—, —OCO—O—, —SO$_2$—, —S—CO—, —CO—S—, —CY1=CY2, or —C≡C— in suitable radicals, and specifically in such a way that the O and/or S atoms are not directly bonded to each other and are likewise optionally substituted with aryl or heteroaryl preferably containing 1 to 30 C atoms (terminal $CH_3$ groups are understood as $CH_2$ groups in the sense of $CH_2$—H).

Compounds having the following structure are preferably used as N-containing carboxylic acid derivatives:

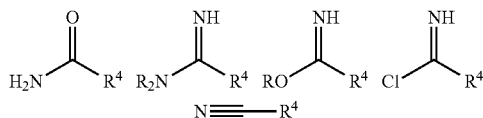

wherein R is selected from among alkyl, aryl, and halogen alkyl, and $R^4$ is selected from the group comprising hydrogen, hydroxyl, halogen, pseudohalogen, formyl, carboxyl and/or carbonyl derivatives, alkyl, long-chain alkyl, alkoxy, long-chain alkoxy, cycloalkyl, halogen alkyl, aryl, arylenes, halogen aryl, heteroaryl, heteroarylenes, heterocycloalkylenes, heterocycloalkyl, halogen heteroaryl, alkenyl, halogen alkenyl, alkinyl, halogen alkinyl, keto, ketoaryl, halogen ketoaryl, ketoheteroaryl, ketoalkyl, halogen ketoalkyl, ketoalkenyl, halogen ketoalkenyl, phosphoalkyl, phosphonates, phosphates, phosphine, phosphine oxide, phosphoryl, phosphoaryl, sulfonyl, sulfoalkyl, sulfoarenyl, sulfonates, sulfates, sulfones, amines, polyether, silylalkyl, silylalkyloxy, wherein one or several of the non-neighboring $CH_2$ groups can be substituted, independently from one another, by means of —O—, —S—, —NH—, —NR°—, —SiR°R°°—, —CO—, —COO—, —OCO—, —OCO—O—, —SO$_2$—, —S—CO—, —CO—S—, —CY1=CY2, or —C≡C— in suitable radicals, and specifically in such a way that the O and/or S atoms are not directly bonded to each other and are likewise optionally substituted with aryl or heteroaryl preferably containing 1 to 30 C atoms (terminal $CH_3$ groups are understood as $CH_2$ groups in the sense of $CH_2$—H).

General Group Definition: General groups, such as, for example: alkyl, alkoxy, aryl, etc., are claimed and described within the description and the claims. The following groups of the generally described groups are preferably utilized within the scope of the invention, unless otherwise described:

Alkyl: linear and branched C1-C8 alkyls.
Long-chain alkyls: linear and branched C5-C20 alkyls
Alkenyl: C2-C6 alkenyl.
Cycloalkyl: C3-C8 cycloalkyl.
Alkoxy: C1-C6 alkoxy.
Long-chain alkoxy: linear and branched C5-C20 alkoxy.
Alkylenes: selected from the group comprising:
methylene; 1,1-ethylene; 1,2-ethylene; 1,1-propylidene; 1,2-propylene; 1,3-propylene; 2,2-propylidene; butane-2-ol-1,4-diyl; propane-2-ol-1,3-diyl; 1,4-butylene; cyclohexane-1,1-diyl; cyclohexane-1,2-diyl; cyclohexane-1,3-diyl; cyclohexane-1,4-diyl; cyclopentane-1,1-diyl; cyclopentane-1,2-diyl; and cyclopentane-1,3-diyl.

Aryl: selected from aromatic compounds with a molecular weight of less than 300 Da.

Arylenes: selected from the group comprising: 1,2-phenylene; 1,3-phenylene; 1,4-phenylene; 1,2-naphthalenylene; 1,3-naphthalenylene; 1,4-napthalenylene; 2,3-naphthalenylene; 1-hydroxy-2,3-phenylene; 1-hydroxy-2,4-phenylene; 1-hydroxy-2,5-phenylene; and 1-hydroxy-2,6-phenylene.

Heteroaryl: selected from the group comprising: pyridinyl; pyrimidinyl; pyrazinyl; triazolyl; pyridazinyl; 1,3,5-triazinyl; quinonyl; isoquinoninyl; quinoxalinyl; imidazolyl; pyrazolyl; benzimidazolyl; thiazolyl; oxazolidinyl; pyrrolyl; thiophenyl; carbazolyl; indolyl; and isoindolyl, wherein the heteroaryl can be bonded to the compound via each atom in the ring of the selected heteroaryl.

Heteroarylenes: selected from the group comprising: pyridindiyl; quinolindiyl; pyrazodiyl; pyrazoldiyl; triazolediyl; pyrazindiyl; thiophendiyl; and imidazolediyl, wherein the heteroarylene functions as a bridge in the compound via a random atom in the ring of the selected heteroaryl, among which are especially preferred: pyridine-2,3-diyl; pyridine-2,4-diyl; pyridine-2,5-diyl; pyridine-2,6-diyl; pyridine-3,4-diyl; pyridine-3,5-diyl; quinoline-2,3-diyl; quinoline-2,4-diyl; quinoline-2,8-diyl; isoquinoline-1,3-diyl; isoquinoline-1,4-diyl; pyrazole-1,3-diyl; pyrazole-3,5-diyl; triazole-3,5-diyl; triazole-1,3-diyl; pyrazine-2,5-diyl; and imidazole-2,4-diyl; thiophene-2,5-diyl; thiophene-3,5-diyl; a —C1-C6-heterocycloalkyl selected from the group comprising: piperidinyl; piperidines; 1,4-piperazines, tetrahydrothiophenes; tetrahydrofurane; 1,4,7-triazacyclononanes; 1,4,8,11-tetraazacyclotetradecanes; 1,4,7,10,13-pentaazacyclopentadecanes; 1,4-diaza-7-thiacyclononanes; 1,4-diaza-7-oxacyclononanes; 1,4,7,10-tetraazacyclododecanes; 1,4-dioxanes; 1,4,7-trithiacyclononanes; pyrrolidines; and tetrahydropyran, wherein the heteroaryl can be bonded to the C1-C6 alkyl via any atom in the ring of the selected heteroaryl.

Heterocycloalkylenes: selected from the group comprising: piperidine-1,2-ylenes; piperidine-2,6-ylenes; piperidine-4,4-ylidenes; 1,4-piperazine-1,4-ylenes; 1,4-piperazine-2,3-ylenes; 1,4-piperazine-2,5-ylenes; 1,4-piperazine-2,6-ylenes; 1,4-piperazine-1,2-ylenes; 1,4-piperazine-1,3-ylenes; 1,4-piperazine-1,4-ylenes; tetrahydrothiophene-2,5-ylenes; tetrahydrothiophene-3,4-ylenes; tetrahydrothiophene-2,3-ylenes; tetrahydrofurane-2,5-ylenes; tetrahydrofurane-3,4-ylenes; tetrahydrofurane-2,3-ylenes; pyrrolidine-2,5-ylenes; pyrrolidine-3,4-ylenes; pyrrolidine-2,3-ylenes; pyrrolidine-1,2-ylenes; pyrrolidine-1,3-ylenes; pyrrolidine-2,2-ylidenes; 1,4,7-triazacyclononane-1,4-ylenes; 1,4,7-triazacyclononane-2,3-ylenes; 1,4,7-triazacyclononane-2,9-ylenes; 1,4,7-triazacyclonon-3,8-ylenes; 1,4,7-triazacyclononane-2,2-ylidenes; 1,4,8,11-tetraazacyclotetradec-1,4-ylenes; 1,4,8,11-tetraazacyclotetradec-1,8-ylenes; 1,4,8,11-tetraazacyclotetradec-2,3-ylenes; 1,4,8,11-tetraazacyclotetradec-2,5-ylenes; 1,4,8,11-tetraazacyclotetradec-1,2-ylenes; 1,4,8,11-tetraazacyclotetradec-2,2-ylidenes; 1,4,7,10-tetraazacyclododec-1,4-ylenes; 1,4,7,10-tetraazacyclododec-1,7-ylenes; 1,4,7,10-tetraazacyclododec-1,2-ylenes; 1,4,7,10-tetraazacyclododec-2,3-ylenes; 1,4,7,10-tetraazacyclododec-2,2-ylidenes; 1,4,7,10,13 pentaazacyclopentadec-1,4-ylenes; 1,4,7,10,13-pentaazacyclopentadec-1,7-ylenes; 1,4,7,10,13-pentaazacyclopentadec-2,3-ylenes; 1,4,7,10,13-pentaazacyclopentadec-1,2-ylenes; 1,4,7,10,13-pentaazacyclopentadec-2,2-ylidenes; 1,4-diaza-7-thiacyclononane-1,4-ylenes; 1,4-diaza-7-thiacyclononane-1,2-ylenes; 1,4-diaza-7-thiacyclononane-2,3-ylenes; 1,4-diaza-7-thiacyclononane-6,8-ylenes; 1,4-diaza-7-thiacyclononane-2,2-ylidenes; 1,4-diaza-7-oxacyclononane-1,4-ylenes; 1,4-diaza-7-oxacyclononane-1,2-ylenes; 1,4-diaza-7-oxacyclononane-2,3-ylenes; 1,4-diaza-7-oxacyclononane-6,8-ylenes; 1,4-diaza-7-oxacyclononane-2,2-ylidenes; 1,4-dioxane-2,3-ylenes; 1,4-dioxane-2,6-ylenes; 1,4-dioxane-2,2-ylidenes; tetrahydropyran-2,3-ylenes; tetrahydropyran-2,6-ylenes; tetrahydropyran-2,5-ylene; tetrahydropyran-2,2-ylidenes; 1,4,7-trithiacyclononane-2,3-ylenes; 1,4,7-trithiacyclononane-2,9-ylenes; and 1,4,7-trithiacyclononane-2,2-ylidenes, Heterocycloalkyl: selected from the group comprising: pyrrolinyl; pyrrolidinyl; morpholinyl; piperidinyl; piperazinyl; hexamethylene imines; 1,4-piperazinyl; tetrahydrothiophenyl; tetrahydrofuranyl; 1,4,7-triazacyclononanyl; 1,4,8,11-tetraazacyclotetradecanyl; 1,4,7,10,13-pentaazacyclopentadecanyl; 1,4-diaza-7-thiacyclononanyl; 1,4-diaza-7-oxacyclononanyl; 1,4,7,10-tetraazacyclododecanyl; 1,4-dioxanyl; 1,4,7-trithiacyclononanyl; tetrahydropyranyl; and oxazolidinyl, wherein the heterocycloalkyl can be bonded to the compound via any atom in the ring of the selected heterocycloalkyl.

Amines: the group —N(R)2, wherein each R is independently selected from among: hydrogen; C1-C6 alkyl; C1-C6 alkyl-C6H5; and phenyl, wherein if both R' are C1-C6 alkyl, both R' can form an —NC3 to NC5 heterocyclic ring, wherein the remaining alkyl chain forms an alkyl substituent on the heterocyclic ring.

Halogen: selected from the group comprising: F; Cl; Br and I.

Halogen alkyl: selected from the group comprising monohalogenated, dihalogenated, trihalogenated, polyhydrogenated, and perhalogenated linear and branched C1-C8 alkyl.

Pseudohalogen: selected from the group comprising: —CH, —SCN, —OCN, N3, —CNO, —SeCN.

Sulfonates: the group —S(O)2OR, wherein R is selected from among: hydrogen; C1-C6 alkyl; phenyl; C1-C6-alkyl-C6H5; Li; Na; K; Cs; Mg; and Ca.

Sulfates: the group —OS(O)2OR, wherein R is selected from among: hydrogen; C1-C6 alkyl; phenyl; C1-C6-alkyl-C6H5; Li; Na; K; Cs; Mg; and Ca.

Sulfones: the group —S(O)2R, wherein R is selected from among: hydrogen; C1-C6 alkyl; phenyl; C1-C6-alkyl-C6H5, and amines (to give sulfonamide) selected from the group: —NR'2, wherein each R' is independently selected from among: hydrogen; C1-C6 alkyl; ClC6-alkyl-C6H5; and phenyl, wherein if both R' are C1-C6 alkyl, both R' can form an —NC3 to NC5 heterocyclic ring, wherein the remaining alkyl chain forms an alkyl substituent on the heterocyclic ring.

Carboxylate: the group —C(O)OR, wherein R is selected from among: hydrogen; C1-C6 alkyl; phenyl; C1-C6-alkyl-C6H5; Li; Na; K; Cs; Mg; and Ca.

Carbonyl: the group —C(O)R, wherein R is selected from among: hydrogen; C1-C6 alkyl; phenyl; C1-C6-alkyl-C6H5, and amines (to give amide) selected from the group: —NR'2, wherein each R' is independently selected from among: hydrogen; C1-C6 alkyl; C1-C6-alkyl-C6H5; and phenyl, wherein if both R' are C1-C6 alkyl, both R' can form an —NC3 to NC5 heterocyclic ring, wherein the remaining alkyl chain forms an alkyl substituent on the heterocyclic ring.

Phosphonates: the group —P(O)(OR)2, wherein each R is independently selected from among: hydrogen; C1-C6 alkyl; phenyl; C1-C6-alkyl-C6H5; Li; Na; K; Cs; Mg; and Ca.

Phosphates: the group —OP(O)(OR)2, wherein each R is independently selected from among: hydrogen; C1-C6 alkyl; phenyl; C1-C6-alkyl-C6H5; Li; Na; K; Cs; Mg; and Ca.

Phosphines: the group —P(R)2, wherein each R is independently selected from among: hydrogen; C1-C6 alkyl; phenyl; and C1-C6-alkyl-C6H5.

Phosphine oxide: the group —P(O)R2, wherein R is independently selected from among: hydrogen; C1-C6 alkyl; phenyl; and C1-C6-alkyl-C6H5; and amines (to give phosphonamidate) selected from the group: —NR'2, wherein each R' is selected from among: hydrogen; C1-C6 alkyl; C1-C6-alkyl-C6H5; and phenyl, wherein if both R' are C1-C6 alkyl, both R' can form an —NC3 to NC5 heterocyclic ring, wherein the remaining alkyl chain forms an alkyl substituent on the heterocyclic ring.

Polyether: selected from the group comprising —(O—CH$_2$—CH(R))$_n$—OH and —(O—CH$_2$—CH(R))$_n$—H, wherein R is selected independently from among: hydrogen, alkyl, aryl, halogen, and n is from 1 to 250.

Silylalkyl: the group —SiR$_3$ wherein each R is selected, independently from one another, from among: hydrogen; C1-C6 alkyl; phenyl; C1-C6-alkyl-C6H5, and amines (to give sulfonamide) selected from the group: —NR'2, wherein each R' is selected from: hydrogen; C1-C6 alkyl; ClC6-alkyl-C6H5; and phenyl, wherein if both R' are C1-C6 alkyl, both R' can form an —NC3 to NC5 heterocyclic ring, wherein the remaining alkyl chain forms an alkyl substituent on the heterocyclic ring.

Silylalkyloxy: the group —OSiR$_3$ wherein each R is selected, independently from one another, from among: hydrogen; C1-C6 alkyl; phenyl; C1-C6-alkyl-C6H5, and amines (to give sulphonamide) selected from the group:

—NR'2, wherein each R' is independently selected from among: hydrogen; C1-C6 alkyl; ClC6-alkyl-C6H5; and phenyl, wherein if both R' are C1-C6 alkyl, both R' can form an —NC3 to NC5 heterocyclic ring, wherein the remaining alkyl chain forms an alkyl substituent on the heterocyclic ring.

The following groups are preferred groups within the general group definition, unless otherwise specified:

Alkyl: linear and branched C1-C6 alkyl.

Long-chain alkyls: linear and branched C5-C10 alkyl, preferably C6-C8 alkyls.

Alkenyl: C3-C6 alkenyl.

Cycloalkyl: C6-C8 cycloalkyl.

Alkoxy: C1-C4 alkoxy.

Long-chain alkoxy: linear and branched C5-C10 alkoxy, preferably linear C6-C8 alkoxy.

Alkylenes: selected from the group comprising: methylenes; 1,2-ethylenes; 1,3-propylenes; butane-2-ol-1,4-diyl; 1,4-butylenes; cyclohexane-1,1-diyl; cyclohexane-1,2-diyl; cyclohexane-1,4-diyl; cyclopentane-1,1-diyl; and cyclopentane-1,2-diyl.

Aryl: selected from the group comprising: phenyl; biphenyl; naphthalenyl; anthracenyl; and phenanthrenyl, Arylene: selected from the group comprising: 1,2-phenylenes; 1,3-phenylenes; 1,4-phenylenes; 1,2-naphthalenylenes; 1,4-naphthalenylenes; 2,3-naphthalenylenes, and 1-hydroxy-2,6-phenylenes.

Heteroaryl: selected from the group comprising: pyridinyl; pyrimidinyl; quinolinyl; pyrazolyl; triazolyl; isoquinoninyl; imidazolyl; and oxazolidinyl, wherein the heteroaryl can be bonded to the compound via any atom in the ring of the selected heteroaryl, Heteroarylenes: selected from the group comprising: pyridine-2,3-diyl; pyridine-2,4-diyl; pyridine-2,6-diyl; pyridine-3,5-diyl; quinoline-2,3-diyl; quinoline-2,4-diyl; isoquinoline-1,3-diyl; isoquinoline-1,4-diyl; pyrazole-3,5-diyl; and imidazole-2,4-diyl.

Heterocycloalkyl: selected from the group comprising: pyrrolidinyl; morpholinyl; piperidinyl; piperidinyl [sic]; 1,4-piperazinyl; tetrahydrofuranyl; 1,4,7-triazacyclononanyl; 1,4,8,11-tetraazacyclotetradecanyl; 1,4,7,10,13-pentaazacyclopentadecanyl; 1,4,7,10-tetraazacyclododecanyl; and piperazinyl, wherein the heteroaryl can be bonded to the compound via any atom in the ring of the selected heteroaryl.

Heterocycloalkylenes: selected from the group comprising: piperidine-2,6-ylenes; piperidine-4,4-ylidenes; 1,4-piperazine-1,4-ylenes; 1,4-piperazine-2,3-ylenes; 1,4-piperazine-2,6-ylenes; tetrahydrothiophene-2,5-ylenes; tetrahydrothiophene-3,4-ylenes; tetrahydrofurane-2,5-ylenes; tetrahydrofurane-3,4-ylenes; pyrrolidine-2,5-ylenes; pyrrolidine-2,2-ylidenes; 1,4,7-triazacyclononane-1,4-ylenes; 1,4,7-triazacyclononane-2,3-ylenes; 1,4,7-triazacyclononane-2,2-ylidenes; 1,4,8,11-tetraazacyclotetradec-1,4-ylenes; 1,4,8,11-tetraazacyclotetradec-1,8-ylenes; 1,4,8,11-tetraazacyclotetradec-2,3-ylenes; 1,4,8,11-tetraazacyclotetradec-2,2-ylidenes; 1,4,7,10-tetraazacyclododec-1,4-ylenes; 1,4,7,10-tetraazacyclododec-1,7-ylenes; 1,4,7,10-tetraazacyclododec-2,3-ylenes; 1,4,7,10-tetraazacyclododec-2,2-ylidenes; 1,4,7,10,13-pentaazacyclopentadec-1,4-ylenes; 1,4,7,10,13-pentaazacyclopentadec-1,7-ylenes; 1,4-diaza-7-thiacyclononane-1,4-ylenes; 1,4-diaza-7-thiacyclononane-2,3-ylenes; 1,4-diaza-7-thiencyclononanee-2,2-ylidenes; 1,4-diaza-7-oxacyclononane-1,4-ylenes; 1,4 diaza-7-oxacyclononane-2,3-ylenes; 1,4-diaza-7-oxacyclononane-2,2-ylidenes; 1,4-dioxane-2,6-ylenes; 1,4-dioxane-2,2-ylidenes; tetrahydropyran-2,6-ylenes; tetrahydropyran-2,5-ylenes; and tetrahydropyran-2,2-ylidenes, a —C1-C6 alkyl heterocycloalkyl, wherein the heteroalkyl is selected from the group comprising: piperidinyl; 1,4-piperazinyl; tetrahydrofuranyl; 1,4,7-triazacyclononanyl; 1,4,8,11-tetraazacyclotetradecanyl; 1,4,7,10,13-pentaazacyclopentadecanyl; 1,4,7,10-tetraazacyclododecanyl; and pyrrolidinyl, wherein the heteroaryl can be bonded to the compound via any atom in the ring of the selected heteroaryl.

Amines: the group —N(R)2, wherein each R is independently selected from among: hydrogen; C1-C6 alkyl; and benzyl.

Halogen: selected from the group comprising: F and Cl.

Sulfonates: the group —S(O)2OR, wherein R is selected from among: hydrogen; C1-C6 alkyl; Na; K; Mg; and Ca.

Sulfates: the group —OS(O)2OR, wherein R is selected from among: hydrogen; C1-C6 alkyl; Na; K; Mg; and Ca.

Sulfones: the group —S(O)2R, wherein R is selected from among: hydrogen; C1-C6 alkyl; benzyl, and amines are selected from the group: —NR'2, wherein each R' independently selected from among: hydrogen; C1-C6 alkyl; and benzyl.

Carboxylate: the group —C(O)OR, wherein R is selected from among: hydrogen; Na; K; Mg; Ca; C1-C6 alkyl; and benzyl.

Carbonyl: the group —C(O)R, wherein R is selected from among: hydrogen; C1-C6 alkyl; benzyl, and amines selected from the group: —NR'2, wherein each R' is independently selected from among: hydrogen; C1-C6 alkyl; and benzyl.

Phosphonates: the group —P(O)(OR)2, wherein each R is independently selected from among: hydrogen; C1-C6 alkyl; benzyl; Na; K; Mg; and Ca.

Phosphates: the group —OP(O)(OR)2, wherein each R is independently selected from among: hydrogen; C1-C6 alkyl; benzyl; Na; K; Mg; and Ca.

Phosphines: the group —P(R)2, wherein each R is independently selected from among: hydrogen; C1-C6 alkyl; and benzyl.

Phosphine oxide: the group —P(O)R2, wherein R is independently selected from among: hydrogen; C1-C6 alkyl; benzyl, and amines selected from the group: —NR'2, wherein each R' is independently selected from among: hydrogen; C1-C6 alkyl; and benzyl.

Polyether: selected from the group comprising —(O—CH$_2$—CH(R))$_n$—OH and —(O—CH$_2$—CH(R))$_n$—H, wherein R is independently selected from among: hydrogen, methyl, halogen, and n is from 5 to 50, preferably 10 to 25.

M, M$_n$ (n is an integer): metals, wherein two metals M are selected, independently from one another, unless otherwise indicated.

Enamines having the following structure are preferably used:

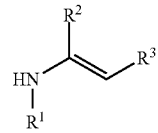

wherein R$^1$ and R$^2$ are as described above, but R$^3$ comprises an electron attracting group, that is, it is selected from the group including formyl, carboxyl and/or carbonyl derivatives, keto, ketoaryl, halogen ketoaryl, ketoheteroaryl, ketoalkyl, halogen ketoalkyl, ketoalkenyl, halogen ketoalkenyl, phosphoalkyl, phosphonates, phosphates, phosphine, phosphine oxide, phosphoryl, phosphoaryl, sulfonyl, sulfoalkyl, sulfoarenyl, sulfonates, sulfates, sulfones, amines, polyether, silylalkyl, silylalkyloxy, wherein one or more non-neighboring $CH_2$ groups can be substituted, independently from one another, by means of —O—, —S—, —NH—, —NR°—, —SiR°R°°—, —CO—, —COO—, —OCO—, —OCO—O—, —$SO_2$—, —S—CO—, —CO—S—, —CY1=CY2, or —C≡C— in suitable radicals, and specifically in such a way that the O and/or S atoms are not directly bonded to each other, likewise optionally replaced with aryl or heteroaryl preferably including 1 to 30 C atoms (terminal $CH_3$-groups are understood as $CH_2$-groups in the sense of $CH_2$—H).

Compounds of this type have shown to be particularly advantageous in the practice, since, on the one hand, the enamines obtained in this way are clearly more stable in general and, on the other hand, the reactivity is frequently greater.

It should be noted at this point that the enamines according to the invention are either used in substance or produced in situ during the conversion depending on the embodiment. This can take place (depending on the embodiment) by converting suitable amines with ketones (if required using dehydrating substances, such as possibly $TiCl_4$ or (if the enamine with the above structure is utilized with an electron attracting group) by means of Michael addition of amine to alkyne.

At this point it should also be noted that—in case nitriles are selected as N-containing carboxylic acid derivatives—they can be used in substance or can be obtained in situ from other carboxylic acid derivatives or suitable precursor substances during the reaction. Suitable precursor substances are in particular those that produce nitriles with dehydrating conditions. In this case—if desired—the enamine as well as the nitrile can be produced in situ during the process.

According to a preferred embodiment of the invention, the conversion is carried out in the presence of a Lewis acid. This has frequently shown to have an accelerating effect on the reaction. The Lewis acid is preferably selected from the group comprising metal ions, preferably with Cu(II), Zn(II), ARM), In(III) salts, as well as protonic acids. Metallic salts are particularly preferred, especially Cu(II) salts, preferably $Cu(OAc)_2$ or $Cu(OAc)_2$ hydrate.

According to a preferred embodiment of the invention, the conversion is carried out in the presence of copper ions.

The Lewis acid, which acts as a catalyst, is preferably used in a ratio of ≥0.1% (mol of catalyst to mol enamine) with reference to the enamine. For the case in which an oxidizing agent is present in addition to the Lewis acid (see below), additional preferred ranges are ≥1% to ≤20%, and even more preferably ≥2% to ≤10%.

According to a preferred embodiment, the oxidizing agent is selected from the group comprising oxygen (or air), ozone, hypohalogenides, in particular hypochlorite, peroxides, metals or metallic salts, or mixtures of these.

Particularly preferred are metallic salts, especially Cu(II) salts, preferably $Cu(OAc)_2$ and $Cu(OAc)_2$ hydrate.

The oxidizing agent is preferably used in a ratio (with reference to the enamine) of ≥1.5:1 to ≤30:1 (mol of oxidizing agent to mol of enamine), even more preferably in a ratio of ≥2:1 to ≤10:1, and even more preferably ≥2.5:1 to ≤3:1.

The use of Cu(II) salts is particularly preferred, in particular for the reason that the copper can simultaneously act as a Lewis acid and will thus have an oxidizing as well as catalytic effect.

The invention is not limited to this, however, but an oxidizing agent can likewise be used in addition to a non-oxidizing Lewis acid.

For the case in which oxygen (or air) is used as oxidizing agent and the reaction is carried out in the presence of a low stoichiometric Lewis acid containing metal ions—preferably Cu(II)—it has been shown in the practice that the yields can again be increased by adding a tertiary or secondary carboxylic acid in the alpha position. This is consequently a preferred embodiment of the invention. In this, α-tertiary carboxylic acids are preferred, such as pivalic acid. In this, the concentration (in mol % with reference to mol of Lewis acid) preferably amounts to >0% to 100%, preferably ≥30% to ≤70%, even more preferably ≥40% to ≤60%, as well as most preferably approximately 50%.

The aforementioned components, as well as those claimed and described in the sample embodiments to be used in accordance with the invention, are not subject to any special exceptions with regard to their size, shape, material selection, and technical concept, so that the selection criteria known in the field of application can be applied without restrictions.

Other details, features, and advantages of the object of the invention can be drawn from the dependent claims as well as from the subsequent description of the corresponding examples, in which several sample embodiments according to the invention process are presented by way of example. These should be understood to be merely of illustrative character.

General Experimental Regulation A (AVV A)

The enamine starter material (1.0 mmol; (Z)-3-(4-fluorophenylamino)-but-2-enoic acid methylester in the case of Example 1) as well as $Cu(OAc)_2$ (3.0 mmol) were weighed in air into a screw-cap vial (with PTFE sealing washer, volume: approximately 7 ml) with magnetic stirring rod stored overnight in a furnace (140° C.). In the case of liquid or oily substrates these were initially diluted with the corresponding solvent, and $Cu(OAc)_2$ was then added, after weighing into the screw-cap vial. The corresponding nitrile (3.0 ml) was added as solvent; the screw-cap vial was firmly sealed and vigorously stirred at room temperature for 1 minute in order to achieve a good suspension of the reaction components. The reaction vessel was then placed in a metal block preheated to 110 or 120° C., and while being stirred its temperature was monitored and regulated via another threaded, oil-filled vial, and was stirred for 14-24 hours. The reaction mixture was removed from the metal block and cooled to room temperature over a period of approximately 15 minutes while stirring. At this time point, the yield and success of the reaction as well as by-product formation were checked with a reaction review per ESI-MS, HPLC-MS, GC-MS, and/or DC (each according to the substrate and product). The reaction mixture was diluted with EtOAc (20 ml), and metal salt precipitates achieved good suspension with thorough stirring. The reaction mixture was then filtered through diatomaceous earth and silica gel (frit diameter: approximately 1.5 cm; filled with approximately 1 cm of sea sand, 2 cm of silica gel, 1 cm of sea sand, 1 cm of diatomaceous earth, 1 cm sea sand, previously eluted with approximately 50 ml of EtOAc), the residue was carefully washed with EtOAc (4×20 ml), and the combined filtrates were released from the solvent in a rotary evaporator under reduced pressure. The raw product was dried in high vacuum, wherein the volatility of the product had to be monitored (in particular with 3,5-dimethyl-substituted products) and, if required, examined by NMR spectroscopy. The raw product was dissolved in $CH_2Cl_2$ (approximately 5 ml), adsorbed on silica gel (approximately 2 g), and purified via column chromatography (silica gel, pentane/EtOAc gradient).

General Experimental Regulation B (AVV B)

The enamine starter material (1.0 mmol; (Z)-3-(4-fluorophenylamino)-but-2-enoic acid methylester in the case of Example 1) as well as Cu(OAc)$_2$ (1.5 mmol) were weighed in air into a screw-cap vial (with PTFE sealing washer, volume: approximately 7 ml) with magnetic stirring rod stored overnight in a furnace (80° C.). In the case of liquid or oily substrates these were initially diluted with the corresponding solvent, and Cu(OAc)$_2$ was then added, after weighing into the screw-cap vial. The corresponding nitrile (1.5 ml) was added as solvent; the screw-cap vial was firmly sealed and vigorously stirred at room temperature for 1 minute in order to achieve a good suspension of the reaction components. The reaction vessel was then placed in a metal block preheated to 110° C., and while being stirred its temperature was monitored and regulated via another threaded, oil-filled vial, and stirred for 24 hours. The reaction mixture was removed from the metal block and cooled to room temperature over a period of approximately 15 minutes while stirring. At this point, the yield and success of the reaction as well as by-product formation were checked with a reaction review per ESI-MS, HPLC-MS, GC-MS and/or DC (each according to the substrate and product). The reaction mixture was diluted with EtOAc (20 ml), and metal salt precipitates achieved good suspension with thorough stirring. The reaction mixture was then filtered through diatomaceous earth and silica gel (frit diameter: approximately 1.5 cm; filled with approximately 1 cm of sea sand, 2 cm of silica gel, 1 cm of sea sand, 1 cm of diatomaceous earth, and 1 cm sea sand, previously eluted with approximately 50 ml of EtOAc), the residue was carefully washed with EtOAc (4×20 ml), and the combined filtrates were released from the solvent in a rotary evaporator under reduced pressure. The raw product was dried in a high vacuum, wherein the volatility of the product had to be monitored (in particular with 3,5-dimethyl-substituted products) and, if required, examined by NMR spectroscopy. The raw product was dissolved in CH$_2$Cl$_2$ (approximately 5 ml), adsorbed on silica gel (approximately 2 g), and purified via column chromatography (silica gel, pentane/EtOAc gradient).

General Experimental Regulation C (AVV C)

The enamine starter material (1.0 mmol/l) as well as Cu(OAc)$_2$ (1.5 mmol) were weighed in air into a screw-cap vial (with PTFE sealing washer, volume: approximately 4 ml) with magnetic stirring rod stored overnight in a furnace (140° C.), followed by the addition of DMF (1 ml) and nitrile (3.0 mmol). In the case of liquid substrates these were initially diluted with the corresponding solvent, and Cu(OAc)$_2$ was then added, after weighing into the screw-cap vial. The screw-cap vial was firmly sealed and vigorously stirred at room temperature for 1 minute, to achieve a good suspension of the reaction components. The reaction vessel was then placed in a metal block preheated to 110° C. and stirred for 24 hours. The reaction mixture was removed from the metal block and cooled to room temperature over a period of approximately 15 minutes while stirring. At this point, the yield and success of the reaction as well as by-product formation were checked with a reaction review per ESI-MS, HPLC-MS, GC-MS, and/or DC (each according to the substrate and product). The reaction mixture was diluted with EtOAc (20 ml), and metal salt precipitates achieved good suspension with thorough stirring. The reaction mixture was then filtered through diatomaceous earth and silica gel (frit diameter: approximately 1.5 cm; filled with approximately 1 cm of sea sand, 2 cm of silica gel, 1 cm of sea sand, 2 cm of diatomaceous earth, and 1 cm sea sand, previously eluted with approximately 50 ml of EtOAc), the residue was carefully washed with EtOAc (4×20 ml), and the combined filtrates were released from the solvent in a rotary evaporator under reduced pressure. The raw product was dissolved in CH$_2$Cl$_2$ (approximately 5 ml), adsorbed on silica gel (approximately 2 g), and purified via column chromatography (silica gel, pentane/EtOAc gradient).

General Experimental Regulation D (AVV D)

The enamine starter material (0.5 mmol) as well as Cu(OAc)$_2$ (0.05 mmol) were weighed in air into a Schlenk flask (volume: approximately 10 ml) with magnetic stirring rod stored overnight in a furnace (140° C.), followed by the addition of 1,2-dichloroethane (DCE, 1 ml), nitrile (0.75 mmol), and then pivalic acid (0.025 mmol, added as 0.4 M original solution in DCE). The lower part containing the compounds was then cooled with liquid nitrogen; the flask was then briefly evacuated and then filled with oxygen (O$_2$). The evacuation and filling with O$_2$ was repeated two more times. The Schlenk flask was sealed and stirred in an oil bath preheated to 110° C. for 24 hours. The reaction mixture was removed from the metal block and cooled to room temperature over a period of approximately 15 minutes while stirring. At this time point, the yield and success of the reaction as well as the by-product formation were checked with a reaction review per ESI-MS, HPLC-MS, GC-MS, and/or DC (each according to the substrate and product). The reaction mixture was diluted with EtOAc (10 ml), and metal salt precipitates achieved good suspension with thorough stirring. The reaction mixture was then filtered through diatomaceous earth and silica gel (frit diameter: approximately 1.5 cm; filled with approximately 0.5 cm of sea sand, 1 cm of silica gel, 0.5 cm of sea sand, previously eluted with approximately 10 ml of EtOAc), the residue was carefully washed with EtOAc (4×10 ml), and the combined filtrates were released from the solvent in a rotary evaporator under reduced pressure. The raw product was dissolved in CH$_2$Cl$_2$ (approximately 5 ml), adsorbed on silica gel (approximately 2 g), and purified via column chromatography (silica gel, pentane/EtOAc gradient).

EXAMPLES

Example 1

Representation of 1-(4-fluorophenyl)-3,5-dimethyl-1H-pyrazole-4-carboxylic acid methylester

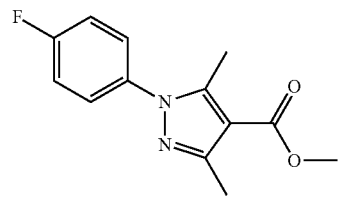 [SMILES: COC(=O)c1c(C)nn(-c2ccc(F)cc2)c1C]

According to AVV A, (Z)-3-(4-fluorophenylamino)-but-2-enoic acid methylester (209.2 mg, 1.0 mmol, 1.0 equiv.) was stirred with Cu(OAc)$_2$ (544.9 mg, 3.0 mmol, 3.0 equiv.) into acetonitrile (3.0 ml, 57.1 mmol, 57.1 equiv.) for 24 hours at 110° C. After purification by means of column chromatography (silica gel (50 g), pentane/EtOAc 95:5→0:100), the product was obtained in the form of a white solid (216.6 mg, 0.87 mmol, 87%).

Alternatively 1-(4-fluorophenyl)-3,5-dimethyl-1H-pyrazole-4-carboxylic acid methylester was obtained according to AVV B with a yield of 84%.

Example 2

Representation of 1-(4-fluorophenyl)-3-trideuteromethyl-5-methyl-1H-pyrazole-4-carboxylic acid methylester

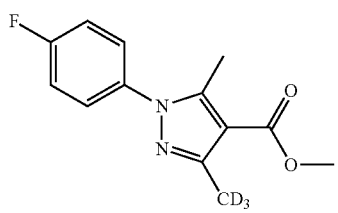 [SMILES: [2H]C([2H])([2H])c1nn(-c2ccc(F)cc2)c(C)c1C(=O)OC]

According to AVV A, (Z)-3-(4-fluorophenylamino)-but-2-enoic acid methylester (209.2 mg, 1.0 mmol, 1.0 equiv.) was stirred with $Cu(OAc)_2$ (544.9 mg, 3.0 mmol, 3.0 equiv.) into $d^3$-acetonitrile (3.0 ml, 57.5 mmol, 57.5 equiv.) for 24 hours at 110° C. After purification by means of column chromatography (diatomaceous earth (50 g), pentane/EtOAc 95:5→0:100), the product was obtained in the form of a white solid (212.2 mg, 0.84 mmol, 84%).

Alternatively 1-(4-fluorophenyl)-3-trideuteromethyl-5-methyl-1H-pyrazole-4-carboxylic acid methylester was obtained according to AVV B with a yield of 85%.

Example 3

Representation of 3-ethyl-1-(4-fluorophenyl)-5-methyl-1H-pyrazole-4-carboxylic acid methylester

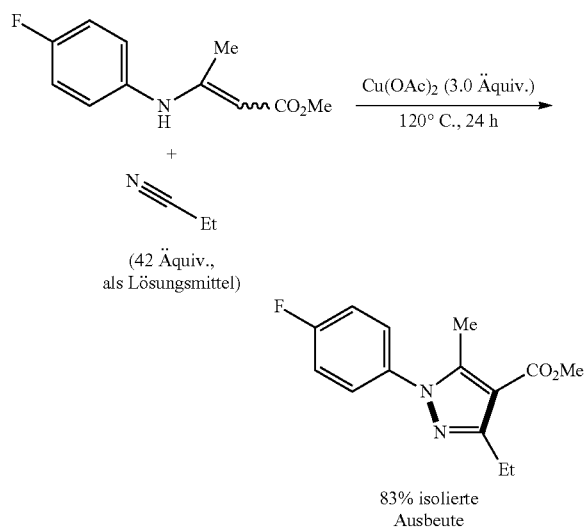

Legends in formula: Äquiv. = Equiv.; als Lösungsmitel = as solvent; isolierte Ausbeute = isolated yield According to AVV A, (Z)-3-(4-fluorophenylamino)-but-2-enoic acid methylester (209.2 mg, 1.0 mmol, 1.0 equiv.) was stirred with $Cu(OAc)_2$ (544.9 mg, 3.0 mmol, 3.0 equiv.) into propionitrile (3.0 ml, 41.9 mmol, 41.9 equiv.) for 24 hours at 120° C. After purification by means of column chromatography (silica gel (50 g), pentane/EtOAc 98:2→70:30→0:100), the product was obtained in the form of a white solid (218.2 mg, 0.83 mmol, 83%).

Alternatively 3-ethyl-1-(4-fluorophenyl)-5-methyl-1H-pyrazole-4-carboxylic acid methylester was obtained according to AVV B with a yield of 77%.

Example 4

Representation of 1-(4-fluorophenyl)-3-isopropyl-5-methyl-1H-pyrazole-4-carboxylic acid methylester

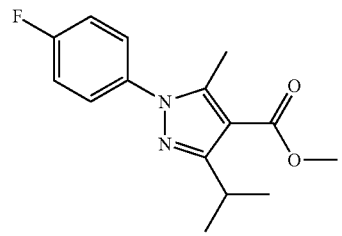 [SMILES: COC(=O)c1c(C(C)C)nn(-c2ccc(F)cc2)c1C]

According to AVV A, (Z)-3-(4-fluorophenylamino)-but-2-enoic acid methylester (209.2 mg, 1.0 mmol, 1.0 equiv.) was stirred with $Cu(OAc)_2$ (544.9 mg, 3.0 mmol, 3.0 equiv.) into isobutyronitrile (3.0 ml, 33.0 mmol, 33.0 equiv.) for 24 hours at 110° C. After purification by means of column chromatography (silica gel (50 g), pentane/EtOAc 98:2→0:100), the product was obtained in the form of a white solid (195.3 mg, 0.71 mmol, 71%).

Alternatively 1-(4-fluorophenyl)-3-isopropyl-5-methyl-1H-pyrazole-4-carboxylic acid methylester was obtained according to AVV B with a yield of 60%.

Example 5

Representation of 1-(4-fluorophenyl)-5-methyl-3-phenyl-1H-pyrazole-4-carboxylic acid methylester

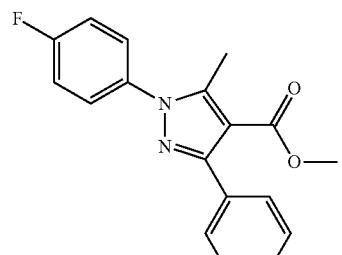

According to AVV A, (Z)-3-(4-fluorophenylamino)-but-2-enoic acid methylester (209.2 mg, 1.0 mmol, 1.0 equiv.) was stirred with $Cu(OAc)_2$ (544.9 mg, 3.0 mmol, 3.0 equiv.) into benzonitrile (3.0 ml, 29.4 mmol, 29.4 equiv.) for 23 hours at 120° C. After purification by means of column chromatography (silica gel (50 g), pentane/EtOAc 98:2→0:100), the product was obtained in the form of a white solid (279.0 mg, 0.90 mmol, 90%).

Alternatively 1-(4-fluorophenyl)-5-methyl-3-phenyl-1H-pyrazole-4-carboxylic acid methylester was obtained according to AVV B with a yield of 80%.

Example 6

Representation of 1-(4-ethoxyphenyl)-3-ethyl-5-methyl-1H-pyrazole-4-carboxylic acid methylester

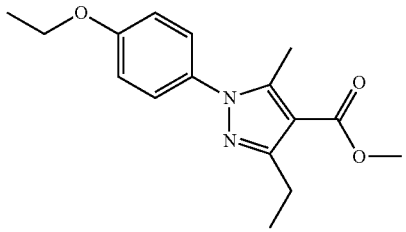 [SMILES: CCOc1ccc(-n2nc(CC)c(C(=O)OC)c2C)cc1]

According to AVV A, (Z-3-(4-ethoxyphenylamino)-but-2-enoic acid methylester (235.3 mg, 1.0 mmol, 1.0 equiv.) was stirred with Cu(OAc)$_2$ (544.9 mg, 3.0 mmol, 3.0 equiv.) into propionitrile (3.0 ml, 41.9 mmol, 41.9 equiv.) for 24 hours at 120° C. The bluish-brown raw product (307.8 mg) was purified by means of column chromatography (silica gel (50 g), pentane/EtOAc 98:2→70:30→0:100), whereby the pure product was obtained in the form of a weak-yellow oil (254.7 mg, 0.88 mmol, 88%).

Alternatively 1-(4-ethoxyphenyl)-3-ethyl-5-methyl-3-phenyl-1H-pyrazole-4-carboxylic acid methylester was obtained according to AVV B with a yield of 83%.

Example 7

Representation of 1-(4-ethoxyphenyl)-5-methyl-3-phenyl-1H-pyrazole-4-carboxylic acid methylester

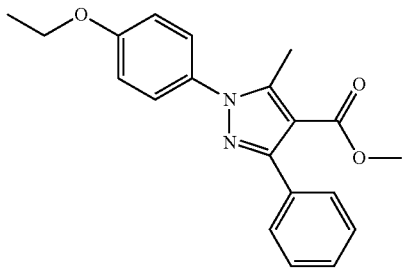 [SMILES: CCOc1ccc(-n2nc(-c3ccccc3)c(C(=O)OC)c2C)cc1]

According to AVV A, (Z-3-(4-ethoxyphenylamino)-but-2-enoic acid methylester (235.3 mg, 1.0 mmol, 1.0 equiv.) was stirred with Cu(OAc)$_2$ (544.9 mg, 3.0 mmol, 3.0 equiv.) into benzonitrile (3.0 ml, 29.4 mmol, 29.4 equiv.) for 14 hours at 120° C. The olive-green oily raw product (490.3 mg) was purified by means of column chromatography (silica gel (50 g), pentane/EtOAc 95:5→0:100). The desired product was obtained in the form of a white solid (291.0 mg, 0.87 mmol, 87%).

Example 8

Representation of 3-ethyl-5-methyl-1-(4-nitrophenyl)-1H-pyrazole-4-carboxylic acid methylester

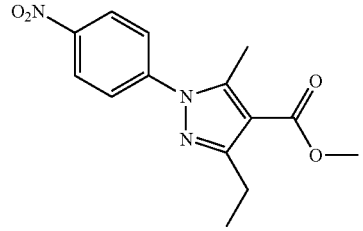 [SMILES: CCc1nn(-c2ccc([N+](=O)[O-])cc2)c(C)c1C(=O)OC]

According to AVV A, (Z-3-(4-nitrophenylamino)-but-2-enoic acid methylester (236.2 mg, 1.0 mmol, 1.0 equiv.) was stirred with Cu(OAc)$_2$ (544.9 mg, 3.0 mmol, 3.0 equiv.) into propionitrile (3.0 ml, 41.9 mmol, 41.9 equiv.) for 21 hours at 120° C. The green solid obtained as raw product 100:0→90:10→0:100), whereby the pure product was obtained in the form of a slightly yellowish solid (188.3 mg, 0.65 mmol, 65%).

Example 9

Representation of 5-methyl-1-(4-nitrophenyl)-3-phenyl-1H-pyrazole-4-carboxylic acid methylester

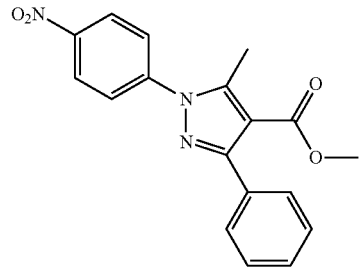 [SMILES: COC(=O)c1c(-c2ccccc2)nn(-c2ccc([N+](=O)[O-])cc2)c1C]

According to AVV A, (Z-3-(4-nitrophenylamino)-but-2-enoic acid methylester (236.2 mg, 1.0 mmol, 1.0 equiv.) was stirred with Cu(OAc)$_2$ (544.9 mg, 3.0 mmol, 3.0 equiv.) into benzonitrile (3.0 ml, 29.4 mmol, 29.4 equiv.) for 14 hours at 120° C. The brown solid obtained as raw product (533.2 mg) was purified by means of column chromatography (silica gel (50 g), CH$_2$Cl$_2$/EtOAc 100:0→90:10→0:100), whereby the pure product was obtained in the form of a slightly yellowish solid (253.5 mg, 0.75 mmol, 75%).

Example 10

Representation of 3-ethyl-5-methyl-1-(2,4,6-trimethylphenyl)-1H-pyrazole-carboxylic acid ethylester

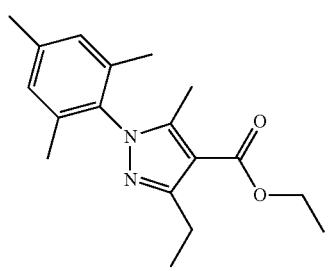 [SMILES: CCOC(=O)c1c(CC)nn(-c2c(C)cc(C)cc2C)c1C]

According to AVV A, (Z-3-(2,4,6-trimethylphenylamino)-but-2-enoic acid ethylester (247.3 mg, 1.0 mmol, 1.0 equiv.) was stirred with Cu(OAc)$_2$ (544.9 mg, 3.0 mmol, 3.0 equiv.) into propionitrile (3.0 ml, 41.9 mmol, 41.9 equiv.) for 20 hours at 120° C. The dark green oil obtained as raw product (333.3 mg) was purified by means of column chromatography (silica gel (25 g), pentane/EtOAc 98:2→0:100). The product was obtained in the form of a yellowish oil (275.3 mg, 0.92 mmol, 92%).

Example 11

Representation of 5-methyl-3-ethyl-1-(2,4,6-trimethylphenyl)-1H-pyrazole-4-carboxylic acid ethylester

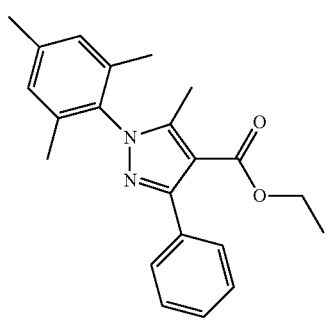 [SMILES: CCOC(=O)c1c(-c2ccccc2)nn(-c2c(C)cc(C)cc2C)c1C]

According to AVV A, (Z-3-(2,4,6-trimethylphenylamino)-but-2-enoic acid ethylester (247.3 mg, 1.0 mmol, 1.0 equiv.) was stirred with Cu(OAc)$_2$ (544.9 mg, 3.0 mmol, 3.0 equiv.) into benzonitrile (3.0 ml, 29.4 mmol, 29.4 equiv.) for 14 hours at 120° C. The brown oil obtained as raw product (524.3 mg) was purified by means of column chromatography (silica gel (50 g), pentane/EtOAc 98:2→0:100). The product was obtained in the form of a white solid (289.4 mg, 0.83 mmol, 83%).

Example 12

Representation of 3-methyl-1-phenyl-1H-pyrazole-4-carboxylic acid methylester

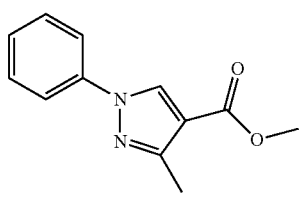 [SMILES: COC(=O)c1cn(-c2ccccc2)nc1C]

According to AVV A, 3-phenylamino acrylic acid methylester (197) (177.2 mg, 1.0 mmol, 1.0 equiv.) was stirred with Cu(OAc)$_2$ (544.9 mg, 3.0 mmol, 3.0 equiv.) into acetonitrile (3.0 ml, 57.1 mmol, 57.1 equiv.) for 22 hours at 110° C. The greenish solid obtained as raw product (242.4 mg) was purified by means of column chromatography (silica gel (50 g), pentane/MTBE 95:5→0:100, then MTBE/EtOAc 100:0→0:100), whereby the desired product was obtained in the form of a yellowish solid (35.1 mg, 0.16 mmol, 16%).

Example 13

Representation of 3-methyl-1-phenyl-1H-pyrazole-4-carboxylic acid methylester

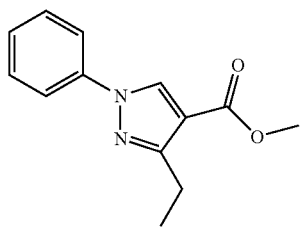 [SMILES: CCc1nn(-c2ccccc2)cc1C(=O)OC]

According to AVV A, 3-phenylamino acrylic acid methylester (177.2 mg, 1.0 mmol, 1.0 equiv.) was stirred with Cu(OAc)$_2$ (544.9 mg, 3.0 mmol, 3.0 equiv.) into propionitrile (3.0 ml, 41.9 mmol, 41.9 equiv.) for 19 hours at 120° C. The orange-brown oily raw product (191.2 mg) was purified by means of column chromatography (silica gel (50 g), pentane/EtOAc 98:2→0:100), whereby the pure product was obtained in the form of a white solid (37.2 mg, 0.16 mmol, 16%).

Example 14

Representation of 1,3-diphenyl-1H-pyrazole-4-carboxylic acid methylester

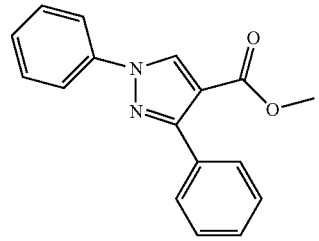 [SMILES: COC(=O)c1cn(-c2ccccc2)nc1-c1ccccc1]

According to AVV A, 3-phenylamino acrylic acid methylester (177.2 mg, 1.0 mmol, 1.0 equiv.) was stirred with Cu(OAc)$_2$ (544.9 mg, 3.0 mmol, 3.0 equiv.) into benzonitrile (3.0 ml, 29.4 mmol, 29.4 equiv.) for 14 hours at 120° C. The green solid (438.1 mg) obtained as raw product was purified by means of column chromatography (silica gel (50 g), pentane/MTBE 95:5→0:100, then MTBE/EtOAc 100:0→0:100). The desired product was obtained in the form of a white solid (108.8 mg, 0.39 mmol, 39%).

Example 15

Representation of 3-methyl-1,5-diphenyl-1H-pyrazole-4-carboxylic acid ethylester

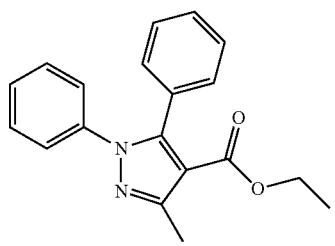 [SMILES: CCOC(=O)c1c(C)nn(-c2ccccc2)c1-c1ccccc1]

According to AVV A, (Z-3-phenyl-3-phenylamino acrylic acid ethylester (267.3 mg, 1.0 mmol, 1.0 equiv.) was stirred with Cu(OAc)₂ (544.9 mg, 3.0 mmol, 3.0 equiv.) into acetonitrile (3.0 ml, 57.1 mmol, 57.1 equiv.) for 21 hours at 110° C. The blue-green raw product (389.3 mg) was purified by means of column chromatography (silica gel (50 g), pentane/EtOAc 98:2→0:100). The product was obtained in the form of a white solid (269.3 mg, 0.88 mmol, 88%).

Example 16

Representation of 3-ethyl-1,5-diphenyl-1H-pyrazole-4-carboxylic acid ethylester

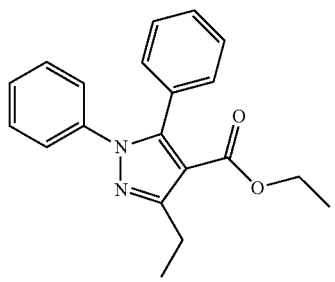 [SMILES: CCOC(=O)c1c(CC)nn(-c2ccccc2)c1-c1ccccc1]

According to AVV A, (Z-3-phenyl-3-phenylamino acrylic acid ethylester (267.3 mg, 1.0 mmol, 1.0 equiv.) was stirred with Cu(OAc)₂ (544.9 mg, 3.0 mmol, 3.0 equiv.) into propionitrile (3.0 ml, 41.9 mmol, 41.9 equiv.) for 24 hours at 120° C. The dark-brown/blue raw product (342.3 mg) was purified by means of column chromatography (silica gel (50 g), pentane/EtOAc 98:2→80:20→0:100). The product was obtained in the form of a white crystalline solid (278.1 mg, 0.87 mmol, 87%).

Alternatively 3-ethyl-1,5-diphenyl-1H-pyrazole-4-carboxylic acid ethylester was obtained according to AVV B with a yield of 80%.

Example 17

Representation of 1,3,5-triphenyl-1H-pyrazole-4-carboxylic acid ethylester

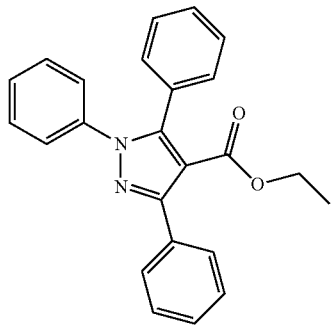 [SMILES: CCOC(=O)c1c(-c2ccccc2)nn(-c2ccccc2)c1-c1ccccc1]

According to AVV A, (Z-3-phenyl-3-phenylamino acrylic acid methylester (267.3 mg, 1.0 mmol, 1.0 equiv.) was stirred with Cu(OAc)₂ (544.9 mg, 3.0 mmol, 3.0 equiv.) into benzonitrile (3.0 ml, 29.4 mmol, 29.4 equiv.) for 14 hours at 120° C. The green solid obtained as raw product (458.2 mg) was purified by means of column chromatography (silica gel (50 g), pentane/EtOAc 95:5→0:100). The product was obtained in the form of a white solid (302.3 mg, 0.82 mmol, 82%).

Example 18

Representation of 3-ethyl-1-(4-fluorophenyl)-5-methyl-1H-pyrazole-4-carboxylic acid tert-butylester

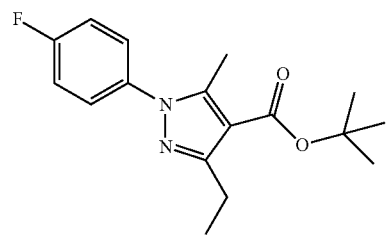 [SMILES: CCc1nn(-c2ccc(F)cc2)c(C)c1C(=O)OC(C)(C)C]

According to AVV A, (Z)-3-(4-fluorophenylamino)-but-2-enoic acid tert-butylester (251.3 mg, 1.0 mmol, 1.0 equiv.) was stirred with Cu(OAc)₂ (544.9 mg, 3.0 mmol, 3.0 equiv.) into propionitrile (3.0 ml, 41.9 mmol, 41.9 equiv.) for 24 hours at 120° C. The dark-brown/blue raw product (295.9 mg) was analyzed by means of $^1$H and $^{19}$F-NMR-spectroscopy. The $^{19}$F-NMR spectra showed the desired product ($\delta=-112.7$ ppm) and N-(4-fluorophenyl)-acetamide ($\delta=-118.0$ ppm) in a ratio of 89:11. After purification by means of column chromatography (silica gel (50 g), pentane/EtOAc 98:2→70:30→0:100), the product was obtained in the form of a yellowish oil (222.9 mg, 0.73 mmol, 73%).

Example 19

Representation of 3-ethyl-1-(4-fluorophenyl)-5-methyl-1H-pyrazole-4-carboxylic acid benzylester

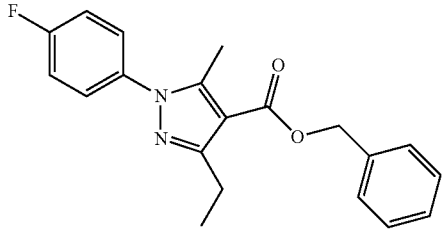 [SMILES: CCc1nn(-c2ccc(F)cc2)c(C)c1C(=O)OCc1ccccc1]

According to AVV A, (Z-3-(4-fluorophenylamino)-but-2-enoic acid benzylester (285.3 mg, 1.0 mmol, 1.0 equiv.) was stirred with Cu(OAc)₂ (544.9 mg, 3.0 mmol, 3.0 equiv.) into propionitrile (3.0 ml, 41.9 mmol, 41.9 equiv.) for 24 hours at 120° C. After purification by means of column chromatography (silica gel (50 g), pentane/EtOAc 98:2→70:30→0:100), the product was obtained in the form of a yellow oil (283.0 mg, 0.84 mmol, 84%).

Example 20

Representation of (3-ethyl-5-methyl-1-phenyl-1H-pyrazole-4-yl)-phenyl methanone

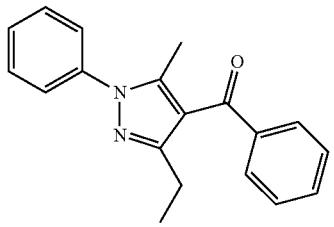 [SMILES: CCc1nn(-c2ccccc2)c(C)c1C(=O)c1ccccc1]

According to AVV A, (Z)-1-phenyl-3-phenylamino-but-2-ene-1-one (237.3 mg, 1.0 mmol, 1.0 equiv.) was stirred with Cu(OAc)$_2$ (544.9 mg, 3.0 mmol, 3.0 equiv.) into propionitrile (3.0 ml, 41.9 mmol, 41.9 equiv.) for 24 hours at 120° C. After the dark-brown bluish raw product (330.0 mg) was purified by means of column chromatography (silica gel (50 g), pentane/EtOAc 98:2→60:40→0:100), the desired product was obtained in the form of a yellow oil (126.2 mg, 0.43 mmol, 43%).

Example 21

Representation of 1-(3-ethyl-5-methyl-1-phenyl-1H-pyrazole-4-yl)-ethanone

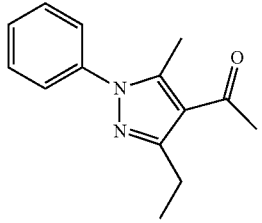 [SMILES: CCc1nn(-c2ccccc2)c(C)c1C(C)=O]

According to AVV A, (Z-4-phenylaminopent-3-ene-2-one (175.2 mg, 1.0 mmol, 1.0 equiv.) was stirred with Cu(OAc)$_2$ (544.9 mg, 3.0 mmol, 3.0 equiv.) into propionitrile (3.0 ml, 41.9 mmol, 41.9 equiv.) for 24 hours at 120° C. After the brown oily raw product (157.3 mg) was purified by means of column chromatography (silica gel (50 g), pentane/EtOAc 94:6→0:100), the desired product was obtained in the form of a yellow oil (57.2 mg, 0.25 mmol, 25%).

Example 22

Representation of 3-ethyl-5-methyl-1-phenethyl-1H-pyrazole-4-carboxylic acid methylester

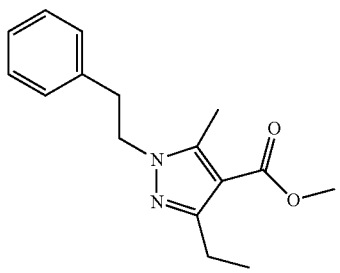 [SMILES: CCc1nn(CCc2ccccc2)c(C)c1C(=O)OC]

According to AVV A, (Z)-3-phenethylamino-but-2-enoic acid methylester (219.3 mg, 1.0 mmol, 1.0 equiv.) was stirred with Cu(OAc)$_2$ (544.9 mg, 3.0 mmol, 3.0 equiv.) into propionitrile (3.0 ml, 41.9 mmol, 41.9 equiv.) for 24 hours at 120° C. The dark brown oil (295.5 mg), obtained as raw product after reprocessing, was purified by means of column chromatography (silica gel (50 g), pentane/EtOAc 98:2→70:30→0:100). The desired product was obtained in the form of a yellow oil (157.8 mg, 0.58 mmol, 58%).

Example 23

Representation of 1-(1-(4-(methoxycarbonyl)-3-ethyl-5-methyl-1H-pyrazole-1-yl)-naphthaline5-yl)-3-ethyl-5-methyl-1H-pyrazole-4-carboxylic acid methylester

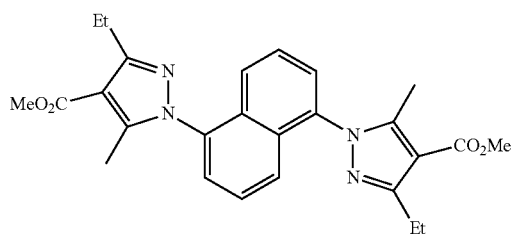 [SMILES: CCc1nn(-c2cccc3c(-n4nc(CC)c(C(=O)OC)c4C)cccc23)c(C)c1C(=O)OC]

According to AVV A, (Z)-3-[5-((Z)-2-methoxycarbonyl-1-methyl-vinylamino)-naphthalene-1-ylamino]-but-2-enoic acid methylester (354.4 mg, 1.0 mmol, 1.0 equiv.) was stirred with Cu(OAc)$_2$ (1.09 mg, 6.0 mmol, 6.0 equiv.) into propionitrile (6.0 ml, 83.9 mmol, 83.9 equiv.) for 16 hours at 120° C. The green-white solid (474.5 mg), obtained as raw product after reprocessing, was purified by means of column chromatography (silica gel (50 g), pentane/EtOAc 93:7→0:100). The desired product was obtained in the form of a white solid (270.1 mg, 0.59 mmol, 59%). A fraction with slightly contaminated product was furthermore isolated in the form of a yellowish solid (58.4 mg, 0.14 mmol, 14%).

Example 24

Representation of 1-(3-(4-(methoxycarbonyl)-3-ethyl-5-methyl-1H-pyrazole-1-yl)phenyl)-3-ethyl-5-methyl-1H-pyrazole-4-carboxylic acid methylester

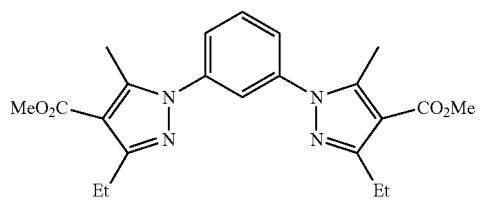 [SMILES: CCc1nn(-c2cccc(-n3nc(CC)c(C(=O)OC)c3C)c2)c(C)c1C(=O)OC]

According to AVV A, (Z)-3-[3-((Z)-2-methoxycarbonyl-1-methyl-vinylamino)-phenylamino]-butenoic acid methylester (213) (304.3 mg, 1.0 mmol, 1.0 equiv.) was stirred with Cu(OAc)$_2$ (1.09 mg, 6.0 mmol, 6.0 equiv.) into propionitrile (6.0 ml, 83.9 mmol, 83.9 equiv.) for 24 hours at 110° C. The brown solid (383.8 mg), obtained as raw product after reprocessing, was purified by means of column chromatography (silica gel (50 g), pentane/EtOAc 94:6→0:100). The desired product was obtained in the form of a white solid (224.7 mg, 0.55 mmol, 55%). A fraction with slightly contaminated product was furthermore isolated in the form of a yellowish solid (63.1 mg, 0.15 mmol, 15%).

Example 25

Representation of 3,5-dimethyl-1-phenyl-1H-pyrazole-4-carboxylic acid ethylester by means of one-pot pyrazole synthesis from aniline and methyl acetoacetate in the 5.0 mmol scale with InBr$_3$ as catalytic Lewis acid

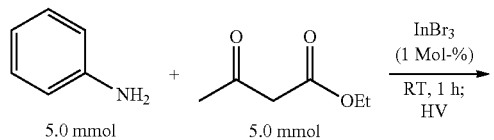

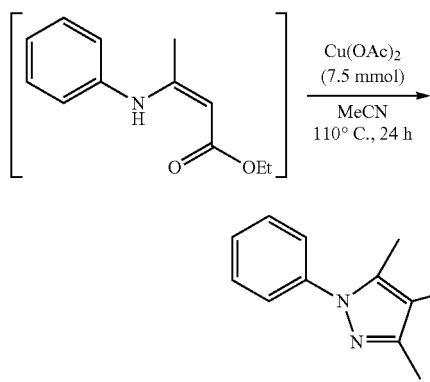

Legend in the formula: Mol-% = mol %.

Legend in the formula: Mol-%=mol %.

InBr$_3$ (17.7 mg, 0.05 mmol, 1 mol %) was weighed in air into a long-neck flask with magnetic stirring rod previously heated in a high vacuum; the flask was evacuated and flooded with argon. Dry aniline (456 µl, 5.0 mmol, 1.0 equiv.) and acetic acid ethylester (632 µl, 5.0 mmol, 1.0 equiv.) were added in the argon return flow, and the reaction mixture was stirred for 1 hour at room temperature. In order to remove the reaction water that was formed, the reaction mixture was evacuated (high vacuum), and the reaction vessel was cooled by immersing it in a bath of liquid nitrogen (−196° C.). After approximately 10 minutes, the cooling bath was removed, and the sample was allowed warm to room temperature. This process (cooling and thawing) was repeated three times. The sample was then kept for another 12 hours under a high vacuum at room temperature and then flooded with argon.

Dry acetonitrile (7.5 ml, 142.7 mmol, 28.6 equiv.) as well as Cu(OAc)$_2$ (1.362 g, 7.5 mmol, 1.5 equiv.) were added under argon, the mixture was stirred vigorously for 1 minute at room temperature, the pressure vessel was sealed, and the reaction mixture was stirred in a preheated oil bath for 24 hours at 110° C. The mixture was cooled to room temperature, diluted with 50 ml of EtOAc, and filtered through diatomaceous earth and silica gel. The residue was carefully washed with EtOAc (3×20 ml). The combined filtrates were released from the solvent in a rotary evaporator under reduced pressure, and the raw product was dried for 10 minutes in a high vacuum. The raw product that was obtained was dissolved in CH$_2$Cl$_2$ (20 ml), adsorbed on silica gel (5 g), and purified by means of column chromatography (silica gel (50 g), pentane/EtOAc 95:5→0:100).

The desired product (3,5-dimethyl-1-phenyl-1H-pyrazole-4-carboxylic acid ethylester) was obtained in the form of a yellowish solid (948.9 mg, 3.88 mmol, 78%), and its analytically obtained data were consistent with those that were previously obtained ant those in the literature.

Example 26

Representation of 5-methyl-1,3-diphenyl-1H-pyrazole-4-carboxylic acid ethylester by means of one-pot pyrazole synthesis from aniline and methyl acetoacetate in the 5.0 mmol scale with InBr$_3$ as catalytic Lewis acid

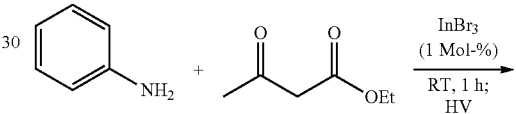

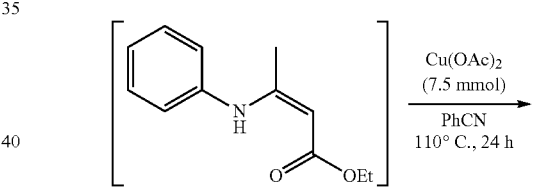

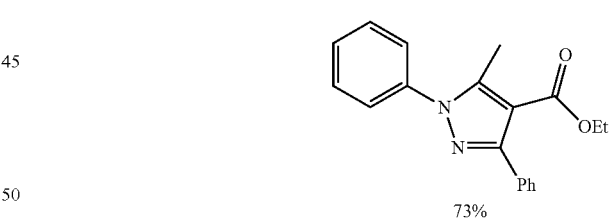

Legend in the formula: Mol-% = mol %.

Legend in the Formula: Mol-%=mol %.

The desired product (5-methyl-1,3-diphenyl-1H-pyrazole-4-carboxylic acid ethylester) was obtained in a yield of 73% (948.3 mg, 3.67 mmol) according to the instruction of Example 25, but utilizing benzonitrile (7.5 ml) instead of acetonitrile.

Examples 27 to 37

The sample compounds 27 through 37 were produced according to AAV C. They were the following compounds:

Example 27

5-methyl-1,3-diphenyl-1H-pyrazole-4-carboxylic acid methylester [Remark: (Z)-3-(phenylamino)-but-2-enoic acid methylester was used as enamine starter material]

Example 28

5-methyl-1-phenyl-3-(m-tolyl)-1H-pyrazole-4-carboxylic acid methylester

Example 29

3-(4-acetylphenyl)-5-methyl-1-phenyl-1H-pyrazole-4-carboxylic acid methylester

Example 30

5-methyl-3-(3-methylpyridin-2-yl)-1-phenyl-1H-pyrazole-4-carboxylic acid methylester

Example 31

3-(furan-2-yl)-5-methyl-1-phenyl-1H-pyrazole-4-carboxylic acid methylester

Example 32

5-methyl-1-phenyl-3-styryl-1H-pyrazole-4-carboxylic acid methylester

Example 33

1,5-dimethyl-3-phenyl-1H-pyrazole-4-carboxylic acid methylester

Example 34

1-butyl-5-methyl-3-phenyl-1H-pyrazole-4-carboxylic acid methylester [Remark: The enamine starter material is liquid.]

Example 35

1-isopropyl-5-methyl-3-phenyl-1H-pyrazole-4-carboxylic acid methylester [Remark: The enamine starter material is liquid.]

Example 36

3-ethyl-5-methyl-1-phenyl-1H-pyrazole-4-carboxylic acid methylester

Example 37

5-methyl-1-phenyl-3-(trifluoromethyl)-1H-pyrazole-4-carboxylic acid methylester

The yields and structural formulas of the products are presented in Table I below.

TABLE I

| Beispiel | Pyrazole | Ausbeute (%)[a] |
|---|---|---|
| 27 | | 72 (213.1 mg, gelber Festsoff) |
| 28 | | 61 (185.5 mg, gelber Festsoff) |
| 29 | | 84 (281.2 mg, gelblicher Festsoff) |
| 30 | | 65 (198.1 mg, gelber Festsoff) |
| 31 | | 77 (218.0 mg, gelber Festsoff) |

TABLE I-continued

| Beispiel | Pyrazole | Ausbeute (%)[a] |
|---|---|---|
| 32 | (1-phenyl-5-methyl-3-styryl-pyrazole-4-carboxylate methyl ester) | 19 (60.3 mg, gelbes Öl) |
| 33 | (1,5-dimethyl-3-phenyl-pyrazole-4-carboxylate methyl ester) | 72[b] (166.0 mg, gelber Festsoff) |
| 34 | (1-butyl-5-methyl-3-phenyl-pyrazole-4-carboxylate methyl ester) | 48 60[b] (162.7 mg,[b] gelbes Öl) |
| 35 | (1-isopropyl-5-methyl-3-phenyl-pyrazole-4-carboxylate methyl ester) | 25 31[b] (79.3 mg,[b] gelbes Öl) |
| 36 | (1-phenyl-3-ethyl-5-methyl-pyrazole-4-carboxylate methyl ester) | 52 (126.4 mg, gelber Festsoff) |
| 37 | (1-phenyl-5-methyl-3-trifluoromethyl-pyrazole-4-carboxylate methyl ester) | 45[c] (32.1 mg, gelber Festsoff) |

Legends in Table I: Beispiel = Example; Pyrazol = Pyrazole; Ausbeute = Yield; gelber Feststoff = Yellow solid; gelblicher Feststoff = Yellowish solid; gelbes Öl = Yellow oil.

[a] Yield of isolated pyrazole product. Isolated amount, color, and consistency in parentheses.

[b] Nitrile (7 equiv.), DMA (N,N-dimethyl acetamide) instead of DMF as solvent.

[c] After all substrates and solvents were added in a Schlenk flask (volume 10 ml for 0.25 mmol formulation), the lower part containing the compounds was cooled to 0° C., the flask was subsequently evacuated, and then filled with trifluoroacetonitrile gas.

Examples 38 through 42

The examples 38 through 42 were produced with the aid of AAV D. They were the following compounds:

Example 38

The same product as in Example 27

Example 39

The same product as in Example 29

Example 40

The same product as in Example 36

Example 41

(5-methyl-1,3-diphenyl-1H-pyrazol-4-yl)(phenyl)methanone

Example 42

The same product as in Example 33

The yields and structural formulas of the products are presented in Table II below.

TABLE II

| Beispiel | Pyrazol | Ausbeute (%)[a] |
|---|---|---|
| 38 | 1,5-diphenyl-3-methyl-pyrazole-4-CO$_2$Me (3-phenyl) | 53 (77.5 mg, gelblicher Festsoff) |
| 39 | 1-phenyl-5-methyl-3-(4-acetylphenyl)-pyrazole-4-CO$_2$Me | 69 (115.3 mg, gelblicher Festsoff) |
| 40 | 1-phenyl-5-methyl-3-ethyl-pyrazole-4-CO$_2$Me | 29 (35.1 mg, gelber Festsoff) |
| 41 | 1,3-diphenyl-5-methyl-4-benzoyl-pyrazole | 48 (81.6 mg, gelblicher Festsoff) |
| 42 | 1,5-dimethyl-3-phenyl-pyrazole-4-CO$_2$Me | 42 (47.8 mg, gelber Festsoff) |

Legends in Table II: Beispiel = Example; Pyrazol = Pyrazole; Ausbeute = Yield; gelblicher-Feststoff = Yellowish solid; gelber Feststoff = Yellow solid
[a] Yield of isolated pyrazole product. Isolated amount, color, and consistency in parentheses.

The individual combinations of components and features of the embodiments already mentioned are meant only as examples; the exchange and substitution of these instructions with other instructions contained in this publication with the publications cited are likewise expressly considered. The technical expert realizes that variations, modifications, and other embodiments described here can likewise occur without deviating from the spirit and scope of the invention. The above-mentioned description is accordingly to be considered as an example and not as a limitation. The word "comprise" used in the claims does not rule out other components or steps. The indefinite article "a/an" does not rule out the meaning of a plural. The mere fact that specific measurements are recited in mutually different claims does not indicate that a combination of these measurements cannot be advantageously utilized. The scope of the invention is defined in the following claims and the corresponding equivalents.

The invention claimed is:

1. A process for the production of pyrazoles by converting enamines and nitriles in the presence of an oxidizing agent.

2. The process according to claim 1, wherein the conversion is carried out in the presence of a Lewis acid.

3. The process according to claim 1, wherein the conversion is carried out in the presence of copper ions.

4. The process according to claim 1, wherein the ratio of enamine to nitrile amounts to ≥0.2:1 to ≤150:1 (mol of nitrile to mol of enamine).

5. The process according to claim 1, wherein the conversion is carried out in the presence of Cu(II) salts and the ratio of enamine to Cu(II) salt is ≥1.5:1 to ≤30:1 (mol of Cu(II) salt to mol of enamine).

* * * * *

UNITED STATES PATENT AND TRADEMARK OFFICE
CERTIFICATE OF CORRECTION

| | | |
|---|---|---|
| PATENT NO. | : 8,716,485 B2 | Page 1 of 3 |
| APPLICATION NO. | : 13/635112 | |
| DATED | : May 6, 2014 | |
| INVENTOR(S) | : Julia Neumann et al. | |

It is certified that error appears in the above-identified patent and that said Letters Patent is hereby corrected as shown below:

In the Specification

COLUMN 9

Line 39, after "Zn(II)," delete "ARM)," and insert -- Al(III), --

COLUMN 14

Line 1, after "AVV A," delete "(Z" and insert -- (Z) --

Line 30, after "AVV A," delete "(Z" and insert -- (Z) --

Line 60, after "AVV A," delete "(Z" and insert -- (Z) --

COLUMN 15

Line 24, after "AVV A," delete "(Z" and insert -- (Z) --

Line 59, after "AVV A," delete "(Z" and insert -- (Z) --

COLUMN 16

Line 15, after "AVV A," delete "(Z" and insert -- (Z) --

Line 19, after "product" insert -- (293.5 mg) was purified by means of column chromatography (silica gel (50 g), $CH_2Cl_2$/EtOAc --

Line 40, after "AVV A," delete "(Z" and insert -- (Z) --

Signed and Sealed this
Fifth Day of August, 2014

Michelle K. Lee
*Deputy Director of the United States Patent and Trademark Office*

COLUMN 17

Line 1, after "AVV A," delete "(Z" and insert -- (Z) --

Line 32, after "AVV A," delete "(Z" and insert -- (Z) --

COLUMN 19

Line 1, after "AVV A," delete "(Z" and insert -- (Z) --

Line 30, after "AVV A," delete "(Z" and insert -- (Z) --

Line 65, after "AVV A," delete "(Z" and insert -- (Z) --

COLUMN 20

Line 60, after "AVV A," delete "(Z" and insert -- (Z) --

COLUMN 21

Line 40, after "AVV A," delete "(Z" and insert -- (Z) --

COLUMN 23

Line 44, delete "Legend in the formula: Mol-%=mol %."

Line 56, delete "Legend in the formula: Mol-%=mol %."

COLUMN 26

TABLE I, Line 7, delete "Festsoff" and insert -- Feststoff --

TABLE I, Line 19, delete "Festsoff" and insert -- Feststoff --

TABLE I, Line 32, delete "Festsoff" and insert -- Feststoff --

TABLE I, Line 47, delete "Festsoff" and insert -- Feststoff --

TABLE I, Line 58, delete "Festsoff" and insert -- Feststoff --

COLUMN 27

TABLE I, Line 22, delete "Festsoff" and insert -- Feststoff --

TABLE I, Line 61, delete "Festsoff" and insert -- Feststoff --

COLUMN 28

TABLE I, Line 10, delete "Festsoff" and insert -- Feststoff --

COLUMN 29

TABLE II, Line 6, delete "Festsoff" and insert -- Feststoff --

TABLE II, Line 18, delete "Festsoff" and insert -- Feststoff --

TABLE II, Line 33, delete "Festsoff" and insert -- Feststoff --

TABLE II, Line 43, delete "Festsoff" and insert -- Feststoff --

COLUMN 30

TABLE II, Line 7, delete "Festsoff" and insert -- Feststoff --